(12) United States Patent
Hansen et al.

(10) Patent No.: US 6,329,367 B1
(45) Date of Patent: Dec. 11, 2001

(54) FUSED 1,2,4-THIADIAZINE DERIVATIVES, THEIR PREPARATION AND USE

(75) Inventors: John Bondo Hansen, Jyderup; Flemming Elmelund Nielsen, Virum, both of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/464,979

(22) Filed: Dec. 16, 1999

Related U.S. Application Data

(60) Provisional application No. 60/115,544, filed on Jan. 12, 1999, and provisional application No. 60/116,438, filed on Jan. 20, 1999.

(30) Foreign Application Priority Data

Dec. 18, 1998 (DK) ............................................. 1998 01693
Jan. 11, 1999 (DK) ............................................. 1999 00018

(51) Int. Cl.[7] ........................ A61K 31/54; C07D 285/16
(52) U.S. Cl. ........................................... 514/222.8; 544/10
(58) Field of Search ............................. 514/222.8; 544/10

(56) References Cited

U.S. PATENT DOCUMENTS 5,889,002 * 3/1999 Nielsen et al. .................... 514/222.8

FOREIGN PATENT DOCUMENTS

WO 97/26265 7/1997 (WO) .
WO 99/03861 1/1999 (WO) .

* cited by examiner

*Primary Examiner*—Mukund J. Shah
*Assistant Examiner*—Tamthom N. Truong
(74) *Attorney, Agent, or Firm*—Reza Green, Esq.; Cheryl H. Agris, Esq.

(57) ABSTRACT

The present invention relates to 4H-thieno[3,2-e]-1,2,4-thiadiazine derivatives of the general formula:

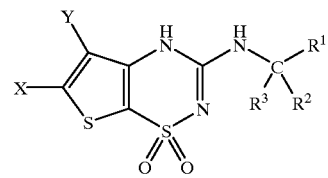

wherein X, Y, $R^1$, $R^2$ and $R^3$ are defined in the description, compositions thereof and methods for preparing the compounds are described.

The compounds are useful in the treatment of diseases of the central nervous system, the cardiovascular system, the pulmonary system, the gastrointestinal system and the endocrinological system.

30 Claims, No Drawings

FUSED 1,2,4-THIADIAZINE DERIVATIVES, THEIR PREPARATION AND USE

CROSS-REFERENCE TO RELATED APPLICATIONS

This application claims priority under 35 U.S.C. 119 of Danish applications PA 1998 01693 filed Dec. 18, 1998 and PA 1999 00018 filed Jan. 11, 1999, and of U.S. Provisional applications No. 60/115,544 filed on Jan. 12, 1999 and No. 60/116,438 filed Jan. 20, 1999, the contents of which are fully incorporated herein by reference.

FIELD OF THE INVENTION

The present invention relates to fused 1,2,4-thiadiazine derivatives, to methods for their preparation, to compositions comprising the compounds, to the use of these compounds as medicaments and their use in therapy e.g. in the treatment or prevention of diseases of the central nervous system, the cardiovascular system, the pulmonary system, the gastrointestinal system and the endocrinological system.

Optionally, the pharmaceutical composition of the invention may comprise a compound of formula I combined with one or more other pharmacologically active compounds, e.g. an antidiabetic or other pharmacologically active material, including compounds for the treatment or prophylaxis of diabetes, including prevention or slowing of progression of impaired fasting glucose (IFG) and impaired glucose tolerance (IGT), as well as insulin resistance and diseases wherein insulin resistance is the pathophysiological mechanism. Suitable antidiabetics comprise short and long acting insulins, insulin analogues as well as orally active hypoglycaemic agents such as sulphonylureas, e.g. glibenclamide and glipizide; biguanides, e.g. mefformin; benzoic acid derivatives, e.g. repaglinide; thiazolidinediones, e.g. troglitazone, rosiglitazone, pioglitazone and ciglitazone; glucagon like peptide 1 (GLP-1), GLP-1 derivatives and GLP-1 analogues; inhibitors of α-glucosidase, e.g. acarbose and voglibose, inhibitors of hepatic enzymes responsible for the biosynthesis of glucose, e.g. glycogen phosphorylase inhibitors.

BACKGROUND OF THE INVENTION

Potassium channels play an important role in the physiological and pharmacological control of cellular membrane potential. Amongst the different types of potassium channels are the ATP-sensitive ($K_{ATP}$-) channels, which are regulated by changes in the intracellular concentration of adenosine triphosphate. The $K_{ATP}$-channels have been found in cells from various tissues such as cardiac cells, pancreatic cells, skeletal muscles, smooth muscles, central neurons and adenohypophysis cells. The channels have been associated with diverse cellular functions for example hormone secretion (insulin from pancreatic beta-cells, growth hormone and prolactin from adenohypophysis cells), vasodilation (in smooth muscle cells), cardiac action potential duration, neurotransmitter release in the central nervous system.

Modulators of the $K_{ATP}$-channels have been found to be of importance for the treatment of various diseases. Certain sulphonylureas, which have been used for the treatment of non-insulin-dependent diabetes mellitus, act by stimulating insulin release through an inhibition of the $K_{ATP}$-channels on pancreatic beta-cells.

The potassium channel openers, which comprise a heterogeneous group of compounds, have been found to be able to relax vascular smooth muscles and have therefore been used for the treatment of hypertension.

In addition, potassium channel openers can be used as bronchodilators in the treatment of asthma and various other diseases.

Furthermore, potassium channel openers have been shown to promote hair growth, and have been used for the treatment of baldness.

Potassium channel openers are also able to relax urinary bladder smooth muscle and therefore, can be used for the treatment of urinary incontinence. Potassium channel openers, which relax smooth muscle of the uterus, can be used for treatment of premature labour.

By acting on potassium channels of the central nervous system these compounds can be used for treatment of various neurological and psychiatric diseases such as Alzheimer, epilepsy and cerebral ischemia.

Further, the compounds are found to be useful in the treatment of benign prostatic hyperplasia, erectile dysfunction and in contraception.

Compounds of the present invention, which inhibit insulin secretion by activating potassium channels of the beta-cell can be used in combination with other compounds which may be used to treat non-insulin dependent diabetes mellitus and insulin dependent diabetes mellitus including prevention or slowing of progression of impaired fasting glucose (IFG) and impaired glucose tolerance (IGT). Examples of such compounds are short and long acting insulins, insulin analogues, insulin sentizers, insulin secretagogues as well as orally active hypoglycaemic agents such as sulphonylureas, e.g. glibenclamide and glipizide; biguanides, e.g. metformin; benzoic acid derivatives, e.g. repaglinide; thiazolidinediones, e.g. troglitazone, rosiglitazone, pioglitazone and ciglitazone; glucagon like peptide 1 (GLP-1), GLP-1 derivatives and GLP-1 analogues; inhibitors of α-glucosidase, e.g. acarbose and voglibose, inhibitors of hepatic enzymes responsible for the biosynthesis of glucose, e.g. glycogen phosphorylase inhibitors.

Since some $K_{ATP}$-openers are able to antagonize vasospasms in basilar or cerebral arteries the compounds of the present invention can be used for the treatment of vasospastic disorders such as subarachnoid haemorrhage and migraine.

Potassium channel openers hyperpolarize neurons and inhibit neurotransmitter release and it is expected that the present compounds can be used for the treatment of various diseases of the central nervous system, e.g. epilepsia, ischemia and neurodegenerative diseases, and for the management of pain.

Recently, it has been shown that diazoxide (7-chloro-3-methyl-2H-1,2,4-benzothiadiazine 1,1-dioxide) and certain 3-(alkylamino)-4H-pyrido[4,3-e]-1,2,4-thiadiazine 1,1-dioxide derivatives inhibit insulin release by an activation of $K_{ATP}$-channels on pancreatic beta-cells (Pirotte B. et al. *Biochem. Pharmacol*, 47, 1381–1386 (1994); Pirotte B. et al., *J. Med. Chem.*, 36, 3211–3213 (1993). Diazoxide has furthermore been shown to delay the onset of diabetes in BB-rats (Vlahos W D et al. *Metabolism* 40, 39–46 (1991)). In obese Zucker rats, diazoxide has been shown to decrease insulin secretion and increase insulin receptor binding and consequently improve glucose tolerance and decrease weight gain (Alemzadeh R. et al. Endocrinol. 133, 705–712, 1993). Compounds, which activate $K_{ATP}$-channels can be used for treatment of diseases characterised by an overproduction of insulin and for the treatment and prevention of diabetes.

EP 618 209 discloses a class of pyridothiadiazine derivatives having an alkyl or an alkylamino group in position 3 of the thiadiazine ring. These compounds are claimed to be agonists at the AMPA-glutamate receptor.

In J. Med. Chem. 1980, 23, 575–577 the synthesis of 4(5)-amino-and formylaminoimidazo-5(4) carboxamide and their properties as agents of chemotherapeutic value are described. Especially, the compounds 3-amino-4,5-dihydro imidazo[4,5-e]-1,2,4-thiadiazine 1,1-dioxide and 3-benzoylamino-4,5-dihydroimidazo[4,5-e]-1,2,4-thiadiazine 1,1-dioxide are shown.

WO 97/26265 discloses a class of fused 1,2,4-thiadiazine and fused 1,4-thiazine derivatives being useful in the treatment of various diseases.

DESCRIPTION OF THE INVENTION

The present invention relates to 4H-thieno[3,2-e]-1,2,4-thiadiazine derivatives of the general formula I:

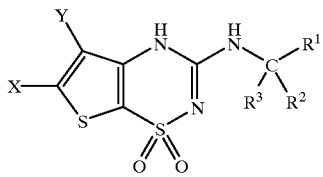

(I)

wherein

X and Y independently are hydrogen, halogen, perhalomethyl, $C_{1-6}$-alkyl or $C_{1-6}$-alkoxy;

$R^1$, $R^2$ and $R^3$ independently are $C_{1-6}$-alkyl, $C_{2-6}$-alkenyl, $C_{2-6}$-alkynyl, $C_{3-6}$-cycloalkyl, carboxy, $C_{1-6}$-alkoxycarbonyl or aryl, all of which are optionally being mono- or polysubstituted with halogen, hydroxy, oxo, or aryl; or $R^1$ is as defined above and $R^2$—C—$R^3$ form $C_{3-6}$-cycloalkyl group, optionally being mono- or polysubstituted with $C_{1-6}$-alkyl, perhalomethyl, halogen, hydroxy or aryl; or —C$R^1R^2R^3$ form a 4- to 12-membered bicyclic or tricyclic carbocyclic system, optionally being mono- or polysubstituted with $C_{1-6}$-alkyl, perhalomethyl, halogen, hydroxy or aryl; or a salt thereof with a pharmaceutically acceptable acid or base.

Within its scope the invention includes all optical isomers of compounds of formula I, some of which are optically active, and also their mixtures including racemic mixture thereof.

The scope of the invention also includes all tautomeric forms of the compounds of formula I as well as metabolites or prodrugs.

A "metabolite" of a compound disclosed in this application is an active derivative of a compound disclosed herein which is produced when the compound is metabolized. Metabolites of compounds disclosed herein can be identified either by administration of a compound to a host and an analysis of blood samples from the host, or by incubation of compounds with hepatic cells in vitro and analysis of the incubant. A "prodrug" is a compound that either is converted into a compound disclosed in the application in vivo or has the same active metabolite as a compound disclosed in this application.

The salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methane-sulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The term "halogen" means fluorine, chlorine, bromine or iodine.

The term "perhalomethyl" means trifluoromethyl, trichloromethyl, tribromomethyl or triiodomethyl.

The terms "$C_{1-6}$-alkyl" as used herein, alone or in combination, refers to a straight or branched, saturated hydrocarbon chain having the indicated number of carbon atoms such as e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-hexyl, 1,2-dimethylpropyl, 2,2-dimethylpropyl, 1,2,2-trimethylpropyl and the like.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "$C_{2-6}$-alkenyl" as used herein refers to an unsaturated hydrocarbon chain having 2–6 carbon atoms and one double bond such as e.g. vinyl, 1-propenyl, allyl, isopropenyl, n-butenyl, n-pentenyl and n-hexenyl.

The term "$C_{2-6}$-alkynyl" as used herein refers to unsaturated hydrocarbons which contain triple bonds, such as e.g. —C≡CH, —C≡CCH$_3$, —CH$_2$C≡CH, —CH$_2$CH$_2$C≡CH, —CH(CH$_3$)C≡CH, and the like.

The term "$C_{1-6}$-alkoxycarbonyl" as used herein refers to a monovalent substituent comprising a $C_{1-6}$-alkoxy group linked through a carbonyl group; such as e.g. methoxycarbonyl, carbethoxy, propoxycarbonyl, isopropoxycarbonyl, n-butoxycarbonyl, sec-butoxycarbonyl, tert-butoxycarbonyl, 3-methylbutoxycarbonyl, n-hexyloxycarbonyl and the like.

The term "$C_{3-6}$-cycloalkyl" as used herein refers to a radical of a saturated cyclic hydrocarbon with the indicated number of carbons such as cyclopropyl, cyclobutyl, cyclopentyl, or cyclohexyl.

The term "aryl" as used herein refers to phenyl, 1-naphthyl, or 2-naphthyl.

The term "4- to 12-membered bicyclic or tricyclic carbocyclic system" as used herein refers to a a monovalent substituent comprising a bicyclic or a tricyclic structure made of 4–12 carbon atoms such as e.g. bicyclo[2.1.1] hexane, bicyclo[2.2.1]heptane, bicyclo[2.2.2]octane, octahydropentalene, bicyclo[2.2.0]hexane, adamantane, noradamantane or tricyclo(4.3.1.1(3,8))undecane.

In one embodiment of the invention X is halogen, e.g. chloro.

In another embodiment of the invention Y is hydrogen.

In another embodiment of the invention $R^1$, $R^2$ and $R^3$ are $C_{1-6}$-alkyl.

In another embodiment of the invention $R^1$ is $C_{1-6}$-alkyl, e.g. methyl or ethyl.

In another embodiment of the invention $R^1$ is carboxy or $C_{1-6}$-alkoxycarbonyl, e.g. carbethoxy.

In another embodiment of the invention $R^1$ is aryl, e.g. phenyl.

In another embodiment of the invention $R^2$—C—$R^3$ form $C_{3-6}$-cycloalkyl group, i.e. a cyclopropyl, cyclobutyl, cyclopentyl or cyclohexyl group.

In another embodiment of the invention —CR$^1$R$^2$R$^3$ form tricyclic carbocyclic system, e.g. adamantane.

Specific compounds of the invention are:

3-tert-Butylamino-6-chloro-4H-thieno[3,2-e]-1,2,4-thiadiazine 1,1-dioxide,
6-Chloro-3-(1,1-dimethylpropylamino)-4H-thieno[3,2-e]-1,2,4-thiadiazine 1,1-dioxide,
6-Chloro-3-(1-methylcyclopropyl)amino-4H-thieno[3,2-e]-1,2,4-thiadiazine 1,1-dioxide,
6-Chloro-3-(2-hydroxy-1,1-dimethylethylamino)-4H-thieno[3,2-e]-1,2,4-thiadiazine 1,1-dioxide,
6-Chloro-3-(1,1,3,3-tetramethylbutylamino)-4H-thieno[3,2-e]-1,2,4-thiadiazine 1,1-dioxide.

Other specific compounds of the invention are:

3-(1-Adamantyl)amino-6-chloro-4H-thieno[3,2-e]-1,2,4-thiadiazine 1,1-dioxide,
1-(6-Chloro-1,4-dihydro-1,1-dioxo-thieno[3,2-e]-1$\lambda^6$,2,4-thiadiazin-3-ylamino)-clopropanecarboxylic acid ethyl ester,
6-Chloro-3-(1-methyl-1-phenylethyl)amino-4H-thieno[3,2-e]-1,2,4-thiadiazine 1,1-dioxide,
6-Chloro-3-(1-hydroxymethylcyclopentyl)amino-4H-thieno[3,2-e]-1,2,4-thiadiazine 1,1-dioxide,
1-(6-Chloro-1,4-dihydro-1,1-dioxo-thieno[3,2-e]-1$\lambda^6$,2,4-thiadiazin-3-ylamino)-cyclopropanecarboxylic acid,
6-Chloro-3-(1-methylcyclobutyl)amino-4H-thieno[3,2-e]-1,2,4-thiadiazine 1,1-dioxide,
6-Chloro-3-(1-methylcyclohexyl)amino-4H-thieno[3,2-e]-1,2,4-thiadiazine 1,1-dioxide,
6-Chloro-3-(1-methylcyclopentyl)amino-4H-thieno[3,2-e]-1,2,4-thiadiazine 1,1-dioxide,
6-Chloro-3-(1-ethylcyclobutyl)amino-4H-thieno[3,2-e]-1,2,4-thiadiazine 1,1-dioxide.

The compounds of the present invention interact with the potassium channels and hence act as openers or blockers of the ATP-regulated potassium channels, which make them useful in the treatment of various diseases of the cardiovascular system, e.g. cerebral ischemia, hypertension, ischemic heart diseases, angina pectoris and coronary heart diseases; the pulmonary system; the gastrointestinal system; the central nervous system and the endocrinological system.

Since some $K_{ATP}$-openers are able to antagonize vasospasms in basilar or cerebral arteries the compounds of the present invention can be used for the treatment of vasospastic disorders such as subarachnoid haemorrhage and migraine.

The compounds of the present invention may also be used for the treatment of diseases associated with decreased skeletal muscle blood flow such as Reynauds disease and intermittent claudication.

Further, the compounds of the invention may be used for the treatment of chronic airway diseases, including asthma, and for treatment of detrusor muscle instability secondary to bladder outflow obstruction and therefore for kidney stones by aiding their passage along the urethra.

The present compounds could also be used for treatment of conditions associated with disturbances in gastrointestinal mobility such as irritable bowel syndrome. Additionally these compounds can be used for the treatment of premature labour and dysmenorrhea.

Potassium channel openers hyperpolarize neurons and inhibit neurotransmitter release and it is expected that such compounds can be used for the treatment of various diseases of the central nervous system, e.g. epilepsia, ischemia and neurodegenerative diseases, and for the management of pain.

Further, potassium channel openers promote hairgrowth, therefore, the compounds of the present invention can be used for the treatment of baldness.

Potassium channel openers also relax urinary bladder smooth muscle, thus, the compounds of the present invention can be used for the treatment of urinary incontinence.

In diseases such as nesidioblastosis and insulinoma in which a hypersecretion of insulin causes severe hypoglycemia the compounds of the present invention can be used to reduce insulin secretion. In obesity hyperinsulinemia and insulin resistance is very frequently encountered. This condition could lead to the development of non-insulin dependent diabetes (NIDDM). Potassium channel openers, and hence the compounds of the present invention, can be used for counteracting the hyperinsulinemia and thereby prevent diabetes and reduce obesity. In overt NIDDM treatment of hyperinsulinemia with potassium channel openers, and hence the present compounds, can be of benefit in restoring glucose sensitivity and normal insulin secretion. Thus, the compounds of the present invention can be used for the treatment of NIDDM.

In early cases of insulin dependent diabetes (IDDM) or in prediabetic cases, potassium channel openers and hence the present compounds can be used to induce pancreatic beta-cell rest which may prevent the progression of the autoimmune disease.

The potassium channel openers of the present invention can be administered in combination with an immunosuppressant or with an agent like nicotinamide, which will reduce autoimmune degeneration of beta-cells.

Combining beta-cell rest with a treatment protecting the beta-cells against cytokine mediated beta-cell impairment/cytotoxicity is another aspect of this invention. Insulin requiring or Type 1 diabetes (IDDM) as well as late onset IDDM (also known as type 1.5. e.g. non-insulin-requiring Type 2 (NIIDM) patients with autoreactivity against beta-cell epitopes that later turns insulin requiring) have circulating autoreactive monocytes/lymphocytes that homes to the islets/beta-cells and releases their cytokines. Some of these cytokines (e.g. interleukin-1b (IL-1b), tumour necrosis factor a (TNFa) and interferon g (IFNg)) are specifically toxic to the beta-cells, e.g. through the induction of nitric oxide (NO) and other free radicals. Inhibition of this cytotoxicity, e.g. by co-administring nicotinamide (NA), a derivative hereof or other cytokine protective compounds to the prediabetic/diabetic patients treated with the PCO compound is an example of this aspect. Nicotinamide belongs to the B-vitamin family and is derived from nicotinic acid by amidation of the carboxyl group. It processes none of nicotine's pharmacological properties. NA is converted into NAD+, which acts as a coenzyme for proteins involved in tissue respiration. NA has been proposed to influence several of the putative intracellular molecular events following immune attack on the beta-cells. Animal experiments and early non-blinded experiments in humans have indicated a protective role of this compound against IDDM as well as in cytokine/immune mediated beta-cell destruction.

Yet another aspect of this application concerns the use of a PCO compound alone or in combination with the inhibitor of cytokine/immune mediated beta-cell impairment, in transplantation, e.g. islet transplantation into diabetes patients. The use of one or both of these treatments may reduce the risk of rejection of the transplanted islets/beta-cells/engineered beta-cells/pancreas.

Compounds of the present invention, which act as blockers of $K_{ATP}$-channels, can be used for the treatment of NIDDM.

The compounds of the present invention may be used for treatment or prevention of diseases of the endocrinological system such as hyperinsulinaemia and diabetes, including prevention or slowing of progression of impaired fasting glucose (IFG) and impaired glucose tolerance (IGT).

Accordingly, in another aspect the invention relates to a compound of the general formula or a pharmaceutically acceptable acid addition salt thereof, for use as a therapeutically acceptable substance, preferably for use as a therapeutically acceptable substance in the treatment of hyperinsulinaemia and treatment or prevention of diabetes, NIDDM and prevention or slowing of progression of impaired fasting glucose (IFG) and impaired glucose tolerance (IGT).

Further, the invention also relates to the use of the inventive compounds of formula I as medicaments useful for treating hyperinsulinaemia and treating or preventing diabetes, NIDDM and prevention or slowing of progression of impaired fasting glucose (IFG) and impaired glucose tolerance (IGT).

Furthermore, the pharmaceutical composition of the invention may comprise a compound of formula I combined with one or more other pharmacologically active compounds, e.g. an antidiabetic or other pharmacologically active material. Suitable antidiabetics comprise short and long acting insulins, insulin analogues as well as orally active hypoglycaemic agents such as sulphonylureas, e.g. glibenclamide and glipizide; biguanides, e.g. metformin; benzoic acid derivatives, e.g. repaglinide; thiazolidinediones, e.g. troglitazone, rosiglitazone, pioglitazone and ciglitazone; glucagon like peptide 1 (GLP-1), GLP-1 derivatives and GLP-1 analogues; inhibitors of α-glucosidase, e.g. acarbose and voglibose, inhibitors of hepatic enzymes responsible for the biosynthesis of glucose, e.g. glycogen phosphorylase inhibitors.

In yet another aspect, the present invention relates to methods of preparing the above mentioned compounds. The methods comprises:

a) reacting a compound of formula II:

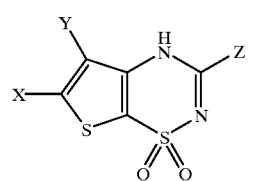

(II)

wherein X and Y are as defined above and Z is a leaving group such as alkoxy, alkylthio, trimethylamino, methylsulfinyl, methylsulfonyl or halogen, preferentially chloro, bromo or iodo, more preferentially fluoro or chloro, with a compound of formula III:

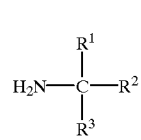

(III)

wherein $R^1$, $R^2$ and $R^3$ are as defined above to form a compound of the general formula I using procedures described by e.g. T. H. Cronon et al., *J.*
*Med. Chem.* 11, 136 (1968); L. Raffa et al., *Farmaco Ed. Sci.* 29, 411 (1974); B. Pirotte et al., *J. Med. Chem.* 36, 3211 (1993);

b) reacting a compound of formula IV:

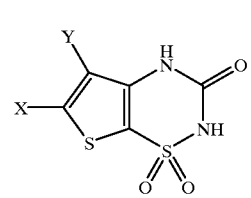

(IV)

wherein X and Y are as defined above, with a compound of formula III, or a suitable salt thereof in the presence of $P_2O_5$ and a high boiling tertiary amine or a suitable salt thereof using a procedure described by Jensen K. G. and Pedersen E. B., *Chem. Scr.*, 20, 248–250 (1988) and Andersen L., Nielsen F. E. and Pedersen E. B., *Chem. Scr.*, 29, 45–49 (1989), to form a compound of the general formula I;

c) reacting a compound of the formula IV:

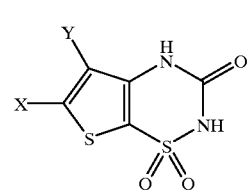

(IV)

wherein X and Y are as defined above, with a compound of formula III, or a suitable salt thereof in the presence of titanium tetrachloride and a solvent with which it may form a complex, like e.g. tetrahydrofuran, or a mixture of toluene and anisole, according to the methods described in R. I. Fryer, J. V. Earley, G. F. Field, W. Zally, and L. H. Sternbach, *J. Org. Chem.* 34, 1143–1145 (1969); J. B. Press et al., *J.Med.Chem.* 22 725–731 (1979); or G. Roma et al. *Eur.J.Med.Chem.* 26, 489–496 (1991), to form a compound of the general formula I;

d) reacting a compound of formula V

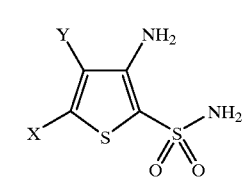

(V)

wherein X and Y are as defined above, with a compound of formula VI

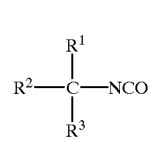

(VI)

wherein $R^1$, $R^2$ and $R^3$ are as defined above using the method described by Chern J. W. et al., *J. Het-* erocycl. Chem., 27, 1909–1915 (1990), to form a compound of the general formula I;

e) reacting a compound of the formula V

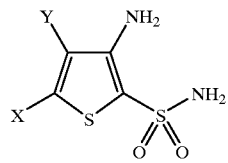
(V)

wherein X and Y are as defined above, with a compound of formula VII

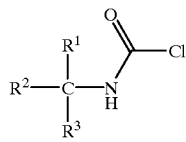
(VII)

wherein $R^1$, $R^2$ and $R^3$ are as above using the method described by Chern J. W. et al., *J. Heterocycl. Chem.*, 27, 1909–1915 (1990), to form a compound of the general formula I;

f) reacting in the presence of a base a compound of formula VIII

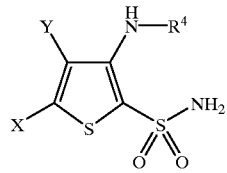
(VII)

or a suitable salt thereof, wherein X and Y are as defined above and $R^4$ is hydrogen or $R^5OC(=O)$, wherein $R^5$ is $C_{1-6}$-alkyl, with a compound of formula IX

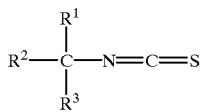
(IX)

wherein $R^1$, $R^2$ and $R^3$ are as defined above, to form an adduct which may have either of the two structures X or XI or be a mixture of the two

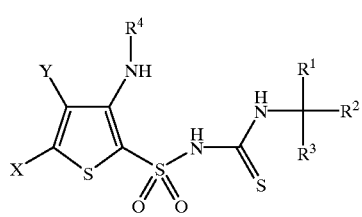
(X)

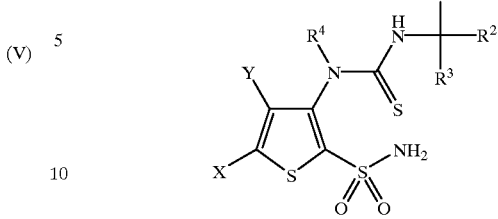
(XI)

either of which by ring-closure, e.g. by treatment with phosgene in a suitable solvent, forms a compound of the general formula I, if $R^4$ is hydrogen, and a compound of the general formula XII if $R^4$ is $R^5OC(=O)$, wherein $R^5$ is $C_{1-6}$-alkyl;

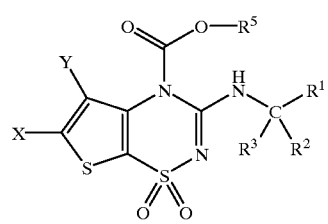
(XII)

g) hydrolyzing and subsequently decarboxylating a compound of the general formula XII

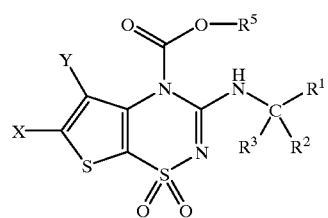
(XII)

to form a compound of the general formula I, e.g. by heating the starting compound in aqueous base.

The starting materials are either known compounds or compounds which may be prepared in analogy with the preparation of known compounds or in analogy with known methods as described by e.g Huang B.-S., et al., *J. Med. Chem.*, 23, 575–7 (1980), Ofitserov V. I. et al., Khim. Geterotsikl. Soedin., 1119–22 (russ.) (1976), Topliss J. G., U.S. Pat. No. 3,641,017 (1972), Kotovskaya S. K. et al., *Khim.-Farm. Zh.*, 13, 54–57 (russ.) (1979), Meyer R. F., *J. Heterocycl. Chem.*, 6, 407–408 (1969) and Hattori M., Yoneda M., and Goto M., *Bull. Chem. Soc. Jap.*, 46, 1890–1 (1973), Williams T. R. and Cram D. J., J. Org. Chem., 38, 20–26 (1973), Barnes A. C., Kennewell P. D. and Taylor J. B., J. Chem. Soc. Chem. Commun., 1973, 776–777, Stoss and Satzinger, Chem. Ber., 109, 2097 (1976), Kresze G., Hatjiissaak A., Phosphorus Sulfur, 29, 41–47 (1987), Dillard R. D., Yen T. T., Stark P., Pavey D. E., J. Med. Chem., 23, 717–722 (1980).

Pharmacological Methods

The ability of the compounds to interact with potassium channels can be determined by various methods. When patch-clamp techniques (Hamill O. P., Marty A., Neher E., Sakmann B. and Sigworth F. J., *Plügers Arch.*, 391, 85–100

(1981)) are used the ionic current through a single channel of a cell can be recorded.

The activity of the compounds as potassium channel openers can also be measured as relaxation of rat aorta rings according to the following procedure:

A section of rat thoracic aorta between the aortic arch and the diaphragm was dissected out and mounted as ring preparations as described by Taylor P. D. et al , *Brit J. Pharmacol*, 111, 42–48 (1994).

After a 45 min. equilibration period under a tension of 2 g, the preparations were contracted to achieve 80% of the maximum response using the required concentration of phenylephrine. When the phenylephrine response reached a plateau, potential vasodilatory agents were added cumulatively to the bath in small volumes using half log molar increments at 2 min intervals. Relaxation was expressed at the percentage of the contracted tension. The potency of a compound was expressed as the concentration required to evoke a 50% relaxation of the tissue.

In the pancreatic beta-cell the opening of the $K_{ATP}$-channels can be determined by measuring the subsequent change in the concentration of cytoplasmic free $Ca^{2+}$ concentration according to the method of Arkhammar P. et al., *J. Biol. Chem.*, 262, 5448–5454 (1987).

The effect of a $K_{ATP}$-channel opener and a $K_{ATP}$-channel blocker on pancreatic beta-cells can be determined by measuring the $^{86}Rb^+$ efflux from a β-cell line according to the following method.

$^{86}Rb^+$ Efflux from a β-cell Line

The RIN 5F cell line was grown in RPMI 1640 with Glutamax I, supplemented with 10% fetal calf serum (from GibcoBRL, Scotland, UK) and maintained in an atmosphere of 5% $CO_2$/95% air at 37° C. The cells were detached with a Trypsin-EDTA solution (from GibcoBRL, Scotland, UK), resuspended in medium, added 1 mCi/ml $^{86}Rb^+$ and replated into microtiter plates (96 well cluster 3596, sterile, from Costar Corporation, MA, USA) at a density of 50000 cells/well in 100 μl/well, and grown 24 hours before use in assay.

The plates were washed 4 times with Ringer buffer (150 mM NaCl, 10 mM Hepes, 3.0 mM KCl, 1.0 mM $CaCl_2$, 20 mM Sucrose, pH 7.1). Eighty μl Ringer buffer and 1 μl control- or test compound dissolved in DMSO was added. After incubation 1 h at room temperature with a lid, 50 μl of the supernatant was transferred to PicoPlates (Packard Instrument Company, CT, USA) and 100 μl MicroScint40 (Packard Instrument Company, CT, USA) added. The plates were counted in TopCount (Packard Instrument Company, CT, USA) for 1 min/well at the $^{32}p$ program.

The calculation of $EC_{50}$ and $E_{max}$ was done by SlideWrite (Advanced Graphics Software, Inc., CA, USA) using a four parameter logistic curve: $y=(a-d)/(1+(x/c)^b)+d$, where a=the activity estimated at concentration zero, b=a slope factor, c=the concentration at the middle of the curve and, d=the activity estimated at infinite concentration. $EC_{50}=c$ and $E_{max}=d$, when the curve is turned of at infinite concentrations.

The effect of $K_{ATP}$-channel modulators on pancreatic beta-cells can be determined by measuring qualitative changes in membrane potential in the insulin producing cell line β-TC3 using fluorescence imaging techniques.

The slow fluorescent membrane potential probe DiBAC was used. The cells were kept in $Ca^{2+}$-HEPES buffer supplemented with 10 mM glucose. After 5 s of each 60 s run the compound was added. 48 wells were run in each set, taking about 1 h. The same cells were then run again, now adding 25 mM KCl after 5 s, and the depolarisation-induced increase in DiBAC fluorescence monitored for 55 s.

In addition the effect of $K_{ATP}$-channel modulators on pancreatic beta-cells can be determined by measuring the increase or decrease in insulin release from insulin producing beta-cell lines or isolated islets.

Effect of $K_{ATP}$-channel modulators can be measured using the following procedure: The beta cells are cultured with change of media every three-four days. Cells are then seeded in 96 well microtiter dishes and cultured for three day at 38° C., 5% $CO_2$ and 95% humidity.

The cells are washed with NN-buffer (+10 mM Hepes+ 0.1% BSA) for one minute and glucose (final conc. 22 mM), IBMX (final conc.0.1 mM) and compounds (final conc. from $5\times10^{-5}$ M–$5\times10^{-8}$ M) added. All cells are then incubated for three hours (38° C., 5% $CO_2$ and 95% humidity).

Supernates are harvested into Greiner minisorb microtiter wells and frozen. Insulin is measured using elisa-techniques.

The compounds of the present invention show high potency in the insulin release test and high selectivity compared to the relaxation of rat aorta rings test.

Pharmaceutical Compositions

The present invention also relates to pharmaceutical compositions comprising, as an active ingredient, at least one of the compounds of the general formula I or a pharmaceutically acceptable salt thereof and, usually, such compositions also contain a pharmaceutically acceptable carrier or diluent.

Pharmaceutical compositions comprising a compound of the present invention may be prepared by conventional techniques, e.g. as described in *Remington: The Science and Practise of Pharmacy*, $19^{th}$ Ed., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier, which may be in the form of a ampoule, capsule, sachet, paper, or other container. When the carrier serves as a diluent, it may be solid, semi-solid, or liquid material, which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, syrup, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similar, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, topical, ophthalmic solution or an oinment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet, appropriate for use in this method, may be prepared by conventional tabletting techniques and contains:

| | |
|---|---|
| Active compound | 5.0 mg |
| Lactosum | 67.8 mg Ph.Eur. |
| Avicel ® | 31.4 mg |
| Amberlite ® | 1.0 mg |
| Magnesii stearas | 0.25 mg Ph.Eur. |

The compounds of the invention may be administered to a mammal, especially a human, in need of such treatment, prevention, elimination, alleviation or amelioration of various diseases as mentioned above and especially of diseases of the endocrinological system such as hyperinsulinaemia and diabetes. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, in an effective amount.

The compounds according to the invention are effective over a wide dose range. For example, in the treatment of humans, dosages from about 0.05 to about 1000 mg, preferably from about 0.1 to about 500 mg of a compound of formula I, conveniently given from 1 to 5 times per day. A most preferable dosage is about 1 mg to about 100 mg per day. The exact dosage will depend upon the mode of administration, form in which administered, the subject to be treated and the body weight of the subject to be treated, and the preference and experience of the physician or veterinarian in charge.

Generally, the compounds are dispensed in unit dosage form comprising from about 1 to about 100 mg of the compounds of formula I in or together with a pharmaceutically acceptable carrier per unit dosage.

Usually, dosage forms suitable for oral, nasal, pulmonal or transdermal administration comprise from about 0.05 mg to about 1000 mg, preferably from about 0.1 mg to about 500 mg of the compounds of formula I admixed with a pharmaceutically acceptable carrier or diluent.

Any novel feature or combination of features described herein is considered essential to this invention.

EXAMPLES

The process of preparing the compounds of formula I is further illustrated in the following examples which, however, are not to be construed as limiting.

Example 1 tert-Butylamino-6-chloro-4H-thieno[3,2-e]-1,2,4-thiadiazine 1,1-dioxide

A solution of 3,6-dichloro-4H-thieno[3,2-e]-1,2,4-thiadiazine 1,1-dioxide (5.0 g, 19.45 mmol) in tert-butylamine (20 ml, 0.19 mol) was stirred for 20 h at 125° C. in a sealed flask. The cooled solution was concentrated in vacuo and the residue was stirred with water (25 ml) followed by adjustment to pH 2 with 4M hydrochloric acid. The resulting precipitate was isolated by filtration, washed with water, and then redissolved in 1 N sodium hydroxide (130 ml) followed by treatment with decolorising charcoal. After filtration, the clear solution was acidified to pH 2 and the precipitate was filtered off and recrystallised from methanol to give 2.91 g (52%) of the pure title compound; mp 368–372° C.; $^1$H-NMR (DMSO-$d_6$): $\delta$1.37 (s, 9H), 6.79 (br s, 1H), 7.11 (s, 1H), 10.55 (br s, 1H); MS: m/e 293/295 (M+); ($C_9H_{12}N_3Cl_1O_2S_2$) calc. C, 36.79; H, 4.12; N, 14.30; Cl, 12.07; S, 21.83; found C, 36.90; H, 4.11; N, 14.18; Cl, 12.05; S, 21.89.

Example 2

6-Chloro-3-(1,1-dimethylpropylamino)-4H-thieno[3,2-e]-1,2,4-thiadiazine 1,1-dioxide A solution of 3,6-dichloro-4H-thieno[3,2-e]-1,2,4-thiadiazine 1,1-dioxide (5.0 g, 19.45 mmol) in 1,1-dimethylpropylamine (10 ml, 85.7 mmol) was stirred for 30 h at 125° C. in a sealed flask. The cooled solution was concentrated in vacuo and the residue was stirred with water (25 ml) followed by adjustment to pH 2 with 4M hydrochloric acid. The resulting precipitate was isolated by filtration, washed with water, and then redissolved by slightly heating in 1N sodium hydroxide (130 ml) followed by treatment with decolorising charcoal. After filtration, the clear solution was acidified to pH 2 and the precipitate was filtered off and recrystallised from methanol to give 3.38 g (56%) of the pure title compound; mp 359–360° C.; $^1$H-NMR (DMSO-$d_6$): $\delta$0.82 (t, 3H), 1.31 (s, 6H), 1,73 (q, 2H), 6.67 (br s, 1H), 7,12 (s, 1H), 10.57 (br s, 1H); MS: m/e 307/309 (M+); ($C_{10}H_{14}N_3Cl_1O_2S_2$) calc. C, 39.02; H, 4.58; N, 13.65; Cl, 11.52; S, 20.83; found C, 39.10; H, 4.58; N, 13.48; Cl, 11.69; S, 20.97.

Example 3

6-Chloro-3-(1-methyl-cyclopropyl)amino-4H-thieno[3,2-e]-1,2,4-thiadiazine 1,1-dioxide A solution of 3,6-dichloro4H-thieno[3,2-e]-1,2,4-thiadiazine 1,1-dioxide (386 mg, 1.5 mmol) in 1-methylcyclopropylamine (1.0 g, 14 mmol) was stirred for 24 h at 85° C. in a sealed flask. The cooled solution was concentrated in vacuo and the residue was stirred with ethyl acetate (1–2 ml) and filtered. The white precipitate was stirred in 4M hydrochloric acid (5 ml) for 2 h and then filtered off and chromatographed on silica gel with ethyl acetate to give 112 mg (26%) of the pure title compound; mp 251–252° C. dec; $^1$H-NMR (DMSO-$d_6$): $\delta$0.65–0.79 (m, 4H), 1.36 (s, 3H), 7.11 (s, 1H), 7.82 (br s, 1H), 10.78 (br s, 1H); MS: m/e 291/293 (M+); ($C_9H_{10}N_3Cl_1O_2S_2$) calc. C, 37.05; H, 3.45; N, 14.40; found C, 36.96; H, 3.53; N, 14.15.

Example 4

6-Chloro-3-(2-hydroxy-1,1-dimethylethylamino)-4H-thieno[3,2-e]-1,2,4-thiadiazine 1,1-dioxide A solution of 3,6-dichloro-4H-thieno[3,2-e]-1,2,4-thiadiazine 1,1-dioxide (0.3 g, 1.17 mmol) in 2-amino-2-methyl-1-propanol (2 ml, 21 mmol) was stirred for 40 h at 120° C. in a sealed flask. Water (5 ml) was added to the cooled solution and pH was adjusted to <2 by the addition of 4M hydrochloric acid. The resulting precipitate was isolated by filtration, washed with water, and recrystallised from methanol/water to give 51 mg (14%) of the pure title compound; mp 224–226° C.; $^1$H-NMR (DMSO-$d_6$): $\delta$1.30 (s, 6H), 3.43 (s, 2H), 5,17 (br s, 1H), 6.63 (br s, 1H), 7.10 (s, 1H), 10.90 (s, 1H); MS: m/e 309/311 (M+).

Example 5

6-Chloro-3-(1,1,3,3-tetramethyl-butylamino)-4H-thieno[3,2-e]-1,2,4-thiadiazine 1,1-dioxide A solution of 3,6-dichloro-4H-thieno[3,2-e]-1,2,4-thiadiazine 1,1-dioxide (0.5 g, 1.95 mm0l) in 1,1,3,3-tetramethylbutylamine (5 ml, 31 mmol) was stirred for 44 h at 120° C. in a sealed flask. Water (25 ml) was added to the cooled solution and pH was adjusted to <2 by the addition of 4M hydrochloric acid. The resulting precipitate was isolated by filtration, washed with water, and then redissolved in 1N sodium hydroxide (15 ml) at 50–60° C. followed by treatment with decolorising charcoal. After filtration, the clear solution was acidified to pH 2 by the addition of 4M hydrochloric acid and the precipitate was filtered off and recrystallised from methanol to give 207 mg (31%) of the pure title compound; mp 369–371° C. dec; $^1$H-NMR (DMSO-$d_6$): $\delta$0.98 (s, 9H), 1.42 (s, 6H), 1,86 (s, 2H), 6.75 (br s, 1H), 7,12 (s, 1H), 10.55 (s, 1H); MS: m/e 349/351 (M+); ($C_{13}H_{20}N_3Cl_1O_2S_2$) calc. C, 44.63; H, 5.76; N, 12.01; found C, 44.74; H, 5.78; N, 11.84.

Example 6

3-(1-Adamantyl)amino-6-chloro-4H-thieno[3,2-e]-1,2,4-thiadiazine 1,1-dioxide

A mixture of 3,6-dichloro-4H-thieno[3,2-e]-1,2,4-thiadiazine 1,1-dioxide (1.0 g, 3.9 mmol), 1-adamantanamine hydrochloride (1.46 g, 7.8 mmol) and triethylamine (1.1 ml, 7.8 mmol) in ethanol (6 ml) was stirred for 41 h at 120° C. in a sealed flask. The cooled solution was concentrated in vacuo and the residue was stirred with water (50 ml) followed by adjustment to pH <2 with 4M hydrochloric acid. The resulting dark mass was isolated by decantation and then partly dissolved in hot 1N sodium hydroxide (50 ml) followed by treatment with decolourising charcoal. After filtration, the solution was acidified to pH <2 and the precipitate was filtered off and recrystallised from ethanol to give 160 mg (11%) of the title compound as a beige solid; mp 339–340° C.; $^1$H-NMR (DMSO-$d_6$): $\delta$1.64 (br s, 6H), 2.02 (br s, 6H), 2.06 (br s, 3H), 6.67 (br s, 1H), 7.10 (s, 1H), 10.55 (br s, 1H); MS: m/e 371/373 (M+); ($C_{15}H_{18}ClN_3O_2S_2$) calc C, 48.44; H, 4.88; N, 11.30; found C, 48.27; H, 4.85; N, 11.15.

Example 7

1-(6-Chloro-1,4-dihydro-1,1-dioxo-thieno[3,2-e]-1$\lambda^6$,2,4-thiadiazin-3-ylamino)-cyclopropanecarboxylic acid ethyl ester A mixture of 3,6-dichloro-4H-thieno[3,2-e]-1,2,4-thiadiazine 1,1-dioxide (1.0 g, 3.9 mmol), 1-aminocyclopropanecarboxylic acid ethyl ester hydrochloride (1.29 g, 7.8 mmol) and triethylamine (1.1 ml, 7.8 mmol) in ethanol (6 ml) was stirred for 23 h at 120° C. in a sealed flask. The cooled solution was concentrated in vacuo and the residue was triturated with water followed by adjustment to pH <2 with 4M hydrochloric acid. The resulting crude dark material was isolated by filtration and purified by chromatography (ethyl acetate) to give 151 mg (11%) of the title compound; mp 190–194° C. (dec.); $^1$H-NMR (DMSO-$d_6$): $\delta$1.15 (t, 3H), 1.22 (m, 2H), 1.50 (m, 2H), 4.09 (q, 2H), 7.06 (s, 1H), 8.14 (br s, 1H), 11.14 (br s, 1H); MS: m/e 349/351 (M+).

Example 8

1-(6-Chloro-1,1-dioxo-1,4-dihydro-thieno[3,2-e]-1$\lambda^6$,2,4-thiadiazin-3-ylamino)-cyclopropanecarboxylic acid A mixture of 3,6-dichloro-4H-thieno[3,2-e]-1,2,4-thiadiazine 1,1-dioxide (1.0 g, 3.9 mmol), 1-aminocyclopropanecarboxylic acid ethyl ester hydrochloride (1.29 g, 7.8 mmol) and triethylamine (1.1 ml, 7.8 mmol) in ethanol (6 ml) was stirred for 23 h at 120° C. in a sealed flask. The cooled solution was concentrated in vacuo and the residue was triturated with water followed by adjustment to pH <2 with 4M hydrochloric acid. The resulting crude dark material was isolated by filtration and boiled in 1N sodium hydroxide followed by treatment with decolourising charcoal. After filtration, the solution was acidified to pH <2 with 4M hydrochloric acid and the precipitate was filtered off and recrystallised from ethanol to give 354 mg (28%) of the title compound; mp 299–300° C. (dec.); $^1$H-NMR (DMSO-$d_6$): $\delta$1.17 (br s, 2H), 1.49 (br s, 2H), 7.09 (s, 1H), 8.1 (br s, 1H), 11.15 (br s, 1H), 12.7 (br s, 1H); MS: m/e 303/305 (M—$H_2O$)$^+$.

Example 9

6-Chloro-3-(1-hydroxymethylcyclopentyl)amino-4H-thieno[3,2-e]-1,2,4-thiadiazine 1,1-dioxide A solution of 3,6-dichloro-4H-thieno[3,2-e]-1,2,4-thiadiazine 1,1-dioxide (0.5 g, 1.95 mmol) and (1-aminocyclopentyl)-methanol (0.45 g, 3.9 mmol) in ethanol (4 ml) was stirred for 21 h at 120° C. in a sealed flask. The cooled solution was concentrated in vacuo and the residue dissolved in 1N sodium hydroxide (40 ml) followed by treatment with decolourising charcoal. After filtration, the clear solution was acidified to pH <2 with 4M hydrochloric acid and the precipitate was filtered off and recrystallised from ethanol and finally purified by chromatography (dichloromethane/methanol (19:1)) to give 70 mg (10%) of the pure title compound; mp 213–214° C.; $^1$H-NMR (DMSO-d$_6$): δ1.45–2.0 (m, 8H), 3.53 (s, 2H), 5.05 (br s, 1H), 6.82 (br s, 1H) 7.11 (s, 1H), 10.8 (br s, 1H); MS: m/e 335/337 (M$^+$), 317/319 (M—H$_2$O)$^+$.

Example 10

6-Chloro-3-(1-methyl-1-phenylethyl)amino-4H-thieno[3,2-e]-1,2,4-thiadiazine 1,1-dioxide A solution of 3,6-dichloro-4H-thieno[3,2-e]-1,2,4-thiadiazine 1,1-dioxide (1.0 g, 3.9 mmol) and cumylamine (1.06 g, 7.8 mmol) in ethanol (6 ml) was stirred for 31 h at 120° C. in a sealed flask. The cooled solution was concentrated in vacuo and the residue dissolved in 1N sodium hydroxide (50 ml) followed by treatment with decolourising charcoal. After filtration, the clear solution was acidified to pH <2 with 4M hydrochloric acid and the precipitate was filtered off and recrystallised from ethanol to give 278 mg (20%) of the title compound; mp ca. 360° C. (decomposes gradually above 200° C.); $^1$H-NMR (DMSO-d$_6$): δ1.68 (s, 6H), 7.12 (s, 1H), 7.17–7.41 (m, 6H), 10.72 (br s, 1H); MS: m/e 355/357 (M$^+$); (C$_{14}$H$_{14}$ClN$_3$O$_2$S$_2$) calc C, 47,25; H, 3.97; N, 11.81; found C, 46.82; H, 3.96; N, 11.62.

Example 11

6-Chloro-3-(1-methylcyclohexyl)amino-4H-thieno[3,2-e]-1,2,4-thiadiazine 1,1-dioxide a) 6-Chloro-3-fluoro-4H-thieno[3,2-e]-1,2,4-thiadiazine 1,1-dioxide

A mixture of 3,6-dichloro-4H-thieno[3,2-e]-1,2,4-thiadiazine 1,1-dioxide (257 mg, 1.0 mmol) and cesium fluoride (456 mg, 3.0 mmol) in dry DMSO (1 ml) was stirred for 16 h at 155° C. in a sealed flask. Water (3 ml) was added to the cooled mixture followed by 4M hydrochloric acid to pH <2. The precipitated beige solid was isolated by filtration, washed with water and dried to give 193 mg (80%) of the title compound; $^1$H-NMR (DMSO-d$_6$): δ7.09 (s, 1H), 7.34 (br s, 1H; MS: m/e 240/242 (M$^+$).

b) 6-Chloro-3-(1-methylcyclohexyl)amino-4H-thieno[3,2-e]-1,2,4-thiadiazine 1,1-dioxide A mixture of 6-chloro-3-fluoro-4H-thieno[3,2-e]-1,2,4-thiadiazine 1,1-dioxide (0.5 g, 2.08 mmol), 1-methylcyclohexylamine hydrochloride (373 mg, 2.49 mmol) and triethylamine (0.58 ml, 4.16 mmol) in ethanol (3 ml) was stirred for 20 h at 50° C. and then for 22 h at 100° C. in a sealed flask. The cooled mixture was concentrated in vacuo and the residue was triturated with water followed by adjustment to pH <2 with 4M hydrochloric acid. The crude product was isolated by filtration and dissolved in 1 N sodium hydroxide followed by treatment with decolourising charcoal. After filtration, the solution was acidified to pH <2 with 4M hydrochloric acid and the precipitate was filtered off and purified by chromatography (dichloromethane/methanol (19:1)). Recrystallisation from ethanol afforded 55 mg (8%) of the pure title compound; mp 218–219° C.; $^1$H-NMR (DMSO-d$_6$): δ1.18–1.54 (m, 11H), 1.97–2.12 (m, 2H), 6.55 (br s, 1H), 7.12 (s, 1H), 10.60 (br s, 1H).

Example 12

6-Chloro-3-(1-methylcyclopentyl)amino-4H-thieno[3,2-e]-1,2,4-thiadiazine 1,1-dioxide A mixture of 6-chloro-3-fluoro-4H-thieno[3,2-e]-1,2,4-thiadiazine 1,1-dioxide (0.60 g, 2.5 mmol), 1-methylcyclopentylamine hydrochloride (0.5 g, 3.7 mmol) and triethylamine (1.03 ml, 7.4 mmol) in ethanol (2.5 ml) was stirred for 16 h at 50° C. and then for 24 h at 65° C. in a sealed flask. The cooled mixture was concentrated in vacuo and the residue was triturated with water followed by adjustment to pH <2 with 1M hydrochloric acid. The crude product was isolated by filtration, dried and recrystallised from acetic acid to give 208 mg (26%) of the title compound; mp >300° C. (dec.); $^1$H-NMR (DMSO-d$_6$): δ1.43 (s, 1H), 1,53–1.72 (m, 6H), 1.92–2.10 (m, 2H), 6.91 (br s, 1H), 7.10 (s, 1H), 10.52 (br s, 1H).

Example 13

6-Chloro-3-(1-methylcyclobutyl)amino-4H-thieno[3,2-e]-1,2,4-thiadiazine 1,1-dioxide A mixture of 6-chloro-3-fluoro-4H-thieno[3,2-e]-1,2,4-thiadiazine 1,1-dioxide (1.3 g, 5.3 mmol), 1-methylcyclobutylamine hydrochloride (1.0 g, 8.1 mmol) and triethylamine (2.5 ml, 18.1 mmol) in ethanol (10 ml) was stirred for 16 h at 50° C. and then for 5 h at 70° C. in a sealed flask. The cooled mixture was concentrated in vacuo and the residue was triturated with water (25 ml) followed by adjustment to pH <2 with 1M hydrochloric acid. The crude product was isolated by filtration, recrystallised from acetic acid and finally purified by chromatography (C18; 20–60% acetonitrile+0.01% TFA) to give 363 mg (22%) of the title compound; mp 294–296° C.; $^1$H-NMR (DMSO-d$_6$): δ1.48 (s, 3H), 1.75–1.88 (m, 2H), 1.94–2.05 (m, 2H), 2.18–2.31 (m, 2H), 7.08 (s, 1H) 7.33 (br s, 1H), 10.67 (br s, 1H); LC-MS: m/e 306/308 (M+1)$^+$.

Example 14

6-Chloro-3-(1-ethylcyclobutyl)amino-4H-thieno[3,2-e]-1,2,4-thiadiazine 1,1-dioxide A mixture of 3,6-dichloro-4H-thieno[3,2-e]-1,2,4-thiadiazine 1,1-dioxide (1.02 g, 3.95 mmol), potassium fluoride (688 mg, 11.9 mmol) and hexadecyltrimethylammonium bromide (43 mg, 0.12 mmol) in dry 1-methyl-2-pyrrolidinone (4 ml) was stirred for 20 h at 130° C. under nitrogen to form 6-chloro-3-fluoro-4H-thieno[3,2-e]-1,2,4-thiadiazine 1,1-dioxide. The mixture was allowed to cool to room temperature and then reacted directly with 1-ethylcyclohexylamine hydrochloride (0.8 g, 5.93 mmol) and triethylamine (1.65 ml, 11.9 mmol) for 30 h at 75° C. in the sealed flask. The cooled mixture was poured into water, acidified to pH <2 with 1N hydrochloric acid and extracted with ethyl acetate. The organic phase was dried with sodium sulphate and evaporated to dryness to give the pure title compound; mp 244–246° C.; $^1$H-NMR (DMSO-d$_6$): δ0.79 (t, 3H), 1.70–1.93 (m, 8H), 1.96–2.08 (m, 2H), 2.13–2.25 (m, 2H), 7.09 (s, 1H), 7.24 (br s, 1 H), 10.57 (br s, 1 H).

What is claimed is:

1. A compound of the general formula I:

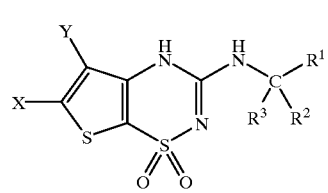

(I)

wherein
- X and Y independently are hydrogen, halogen, perhalomethyl, $C_{1-6}$-alkyl or $C_{1-6}$-alkoxy;
- $R^1$, $R^2$ and $R^3$ independently are $C_{1-6}$-alkyl, $C_{2-6}$-alkenyl, $C_{2-6}$-alkynyl, $C_{3-6}$-cycloalkyl, carboxy, $C_{1-6}$-alkoxycarbonyl or aryl, all of which are optionally being mono- or polysubstituted with halogen, hydroxy, oxo, or aryl; or
- $R^1$ is as defined above and $R^2$—C—$R^3$ form a $C_{3-6}$-cycloalkyl group, optionally being mono- or polysubstituted with $C_{1-6}$-alkyl, perhalomethyl, halogen, hydroxy or aryl; or
- —$CR^1R^2R^3$ form a 4- to 12-membered bicyclic or tricyclic carbocyclic system, optionally being mono- or polysubstituted with $C_{1-6}$-alkyl, perhalomethyl, halogen, hydroxy or aryl; or
- a salt thereof with a pharmaceutically acceptable acid or base including all optical isomers of compounds of formula I, some of which are optically active, and also their mixtures including racemic mixtures, or any tautomeric form thereof.

2. A compound according to claim 1 wherein X is halogen and Y is hydrogen.

3. A compound according to claim 2 wherein X is chloro.

4. A compound according to claim 1 wherein $R^1$, $R^2$ and $R^3$ all are $C_{1-6}$-alkyl.

5. A compound according to claim 1 wherein $R^1$ is $C_{1-6}$-alkyl.

6. A compound according to claim 5 wherein $R^1$ is methyl.

7. A compound according to claim 1 wherein $R^2$—C—$R^3$ forms a $C_{3-6}$-cycloalkyl group.

8. A compound according to claim 1 wherein —$CR^1R^2R^3$ forms a tricyclic carbocyclic system.

9. A compound according to claim 1 wherein the $C_{1-6}$alkyl-group is substituted with hydroxy.

10. A compound according to claim 1 selected from the following:

3-tert-Butylamino-6-chloro-4H-thieno[3,2-e]-1,2,4-thiadiazine 1,1-dioxide;
6-Chloro-3-(1,1-dimethylpropylamino)-4H-thieno[3,2-e]-1,2,4-thiadiazine 1,1-dioxide;
6-Chloro-3-(1-methylcyclopropyl)amino-4H-thieno[3,2-e]-1,2,4-thiadiazine 1,1-dioxide;
6-Chloro-3-(2-hydroxy-1,1-dimethylethylamino)-4H-thieno[3,2-e]-1,2,4-thiadiazine 1,1-dioxide;
6-Chloro-3-(1,1,3,3-tetramethylbutylamino)-4H-thieno[3,2-e]-1,2,4-thiadiazine 1,1-dioxide; or a salt thereof with a pharmaceutically acceptable acid or base including all optical isomers of compounds of formula I, some of which are optically active, and also their mixtures including racemic mixtures, or any tautomeric form thereof.

11. A compound according to claim 1 selected from the group consisting of:

3-(1-Adamantyl)amino-6-chloro-4H-thieno[3,2-e]-1,2,4-thiadiazine 1,1-dioxide;
1-(6-Chloro-1,4-dihydro-1,1-dioxo-thieno[3,2-e]-1$\lambda^6$,2,4-thiadiazin-3-ylamino)-cyclopropanecarboxylic acid ethyl ester;
6-Chloro-3-(1-methyl-1-phenylethyl)amino-4H-thieno[3,2-e]-1,2,4-thiadiazine 1,1-dioxide;
6-Chloro-3-(1-hydroxymethylcyclopentyl)amino-4H-thieno[3,2-e]-1,2,4-thiadiazine 1,1-dioxide;
1-(6-Chloro-1,4-dihydro-1,1-dioxo-thieno[3,2-e]-1$\lambda^6$,2,4-thiadiazin-3-ylamino)-cyclopropanecarboxylic acid;
6-Chloro-3-(1-methylcyclobutyl)amino-4H-thieno[3,2-e]-1,2,4-thiadiazine 1,1-dioxide;
6-Chloro-3-(1-methylcyclohexyl)amino-4H-thieno[3,2-e]-1,2,4-thiadiazine 1,1-dioxide;
6-Chloro-3-(1-methylcyclopentyl)amino-4H-thieno[3,2-e]-1,2,4-thiadiazine 1,1-dioxide;
6-Chloro-3-(1-ethylcyclobutyl)amino-4H-thieno[3,2-e]-1,2,4-thiadiazine 1,1-dioxide; or a salt thereof with a pharmaceutically acceptable acid or base including all optical isomers of compounds of formula I, some of which are optically active, and also their mixtures including racemic mixtures, or any tautomeric form thereof.

12. A composition comprising the compound of claim 1 together with a pharmaceutically acceptable carrier or diluent.

13. The composition according to claim 12 in the form of an oral dosage unit or parenteral dosage unit.

14. A method for opening $K_{ATP}$ regulated potassium channels in a subject comprising administering to said subject in need thereof an amount of the compound of claim 1 effective to open $K_{ATP}$ regulated potassium channels in said subject.

15. A method for opening $K_{ATP}$ regulated potassium channels in a subject in need thereof comprising administering to said subject an amount of the composition of claim 12 effective to open $K_{ATP}$ regulated potassium channels in said subject.

16. The method according to claim 15, in which said $K_{ATP}$ regulated potassium channels are opened in pancreatic beta cells.

17. A method for treating diseases of the endocrinologic system comprising administering to a subject in need thereof an effective amount of the compound of claim 1.

18. A method for treating diseases of the endocrinologic system comprising administering to a subject in need thereof an effective amount of the composition of claim 12.

19. The method according to claim 18, wherein the composition is administered as a dose ranging from about 0.05 mg to 1000 mg per day.

20. The method according to claim 19, wherein the dose ranges from about 0.1 mg to 500 mg per day.

21. The method according to claim 19, wherein the dose ranges from about 50 mg to 200 mg per day.

22. The method according to claim 19, in which the disease of the endocrinologic system is diabetes.

23. The method according to claim 22, in which the diabetes is non-insulin dependent diabetes mellitus.

24. The method according to claim 19, in which the disease of the endocrinologic system is selected from the group consisting of impaired fasting glucose, impaired glucose tolerance and hyperinsulinemia.

25. A method for preparing the compound of claim 1 comprising:

reacting a compound of formula II or formula IV (II)

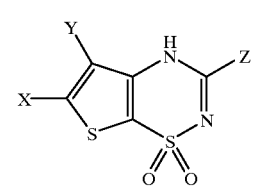

(IV)

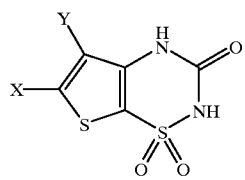

wherein X and Y are independently hydrogen, halogen, perhalomethyl, $C_{1-6}$-alkyl or $C_{1-6}$-alkoxy and Z is a leaving group selected from the group consisting of alkoxy, alkythio, trimethylamino, methylsulfinyl, methylsulfonyl and halogen, with a compound of formula III (III)

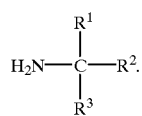

wherein $R^1$, $R^2$ and $R^3$ independently are $C_{1-6}$-alkyl, $C_{2-6}$-alkenyl, $C_{2-6}$-alkynyl, $C_{3-6}$-cycloalkyl, carboxy, $C_{1-6}$-alkoxycarbonyl or aryl, all of which are optionally being mono- or polysubstituted with halogen, hydroxy, oxo or aryl; or $R^1$ is defined above and $R^2$—C—$R^3$ form a $C_{-3-6}$ cycloalkyl group, optionally being mono- or polysubstituted with $C_{1-6}$-alkyl, perhalomethyl, halogen, hydroxy or aryl; or $CR^1 R^2 R^3$ form a 4- to 12-membered bicyclic or tricyclic carbocyclic system, optionally being mono- or polysubstituted with $C_{1-6}$-alkyl, perhalomethyl, halogen, hydroxy or aryl to form the compound of claim 1, wherein when the compound of formula IV is reacted with the compound of formula III said reaction occurs in the presence of $P_2O_5$ and a high boiling tertiary amino or a suitable salt thereof or in the presence of titanium tetrachloride and a solvent to form a complex.

26. The method according to claim 25, wherein Z is chloro, fluoro, bromo or iodo.

27. A method for preparing the compound of claim 1 comprising reacting a compound of formula V (V)

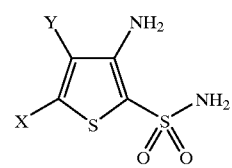

wherein wherein X and Y are independently hydrogen, halogen, perhalomethyl, $C_{1-6}$-alkyl or $C_{1-6}$-alkoxy with a compound of formula VI or VII (VI)

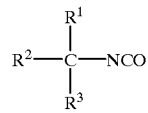

(VII)

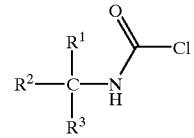

wherein $R^1$, $R^2$ and $R^3$ independently are $C_{1-6}$-alkyl, $C_{2-6}$-alkenyl, $C_{2-6}$-alkynyl, $C_{3-6}$-cycloalkyl, carboxy, $C_{1-6}$-alkoxycarbonyl or aryl, all of which are optionally being mono- or polysubstituted with halogen, hydroxy, oxo or aryl; or $R^1$ is defined above and $R^2$—C—$R^3$ form a $C_{-3-6}$ cycloalkyl group, optionally being mono- or polysubstituted with $C_{1-6}$-alkyl, perhalomethyl, halogen, hydroxy or aryl; or $CR^1R^2R^3$ form a 4- to 12-membered bicyclic or tricyclic carbocyclic system, optionally being mono- or polysubstituted with $C_{1-6}$-alkyl, perhalomethyl, halogen, hydroxy or aryl to form the compound of claim 1.

28. A method for preparing the compound of claim 1 comprising
(a) reacting a compound of formula VIII (VIII)

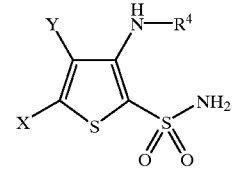

wherein X and Y are independently hydrogen, halogen, perhalomethyl, $C_{1-6}$-alkyl or $C_{1-6}$-alkoxy and $R^4$ is hydrogen or $R^5$ is $C_{1-6}$-alkyl with a compound of formula IX (IX)

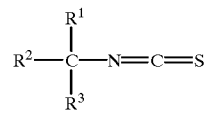

wherein $R^1$, $R^2$ and $R^3$ independently are $C_{1-6}$-alkyl, $C_{2-6}$-alkenyl, $C_{2-6}$-alkynyl, $C_{3-6}$-cycloalkyl, carboxy, $C_{1-6}$-alkoxycarbonyl or aryl, all of which are optionally being mono- or polysubstituted with halogen, hydroxy, oxo or aryl; or $R^1$ is defined above and $R^2$—C—$R^3$ form a $C_{-3-6}$ cycloalkyl group, optionally being mono- or polysubstituted with $C_{1-6}$-alkyl, perhalomethyl, halogen, hydroxy or aryl; or $CR^1R^2R^3$ form a 4- to 12-membered bicyclic or tricyclic carbocyclic system, optionally being mono- or polysubstituted with $C_{1-6}$-alkyl, perhalomethyl, halogen, hydroxy or aryl to form an adduct which may have either of the two structures X or XI or mixtures thereof;

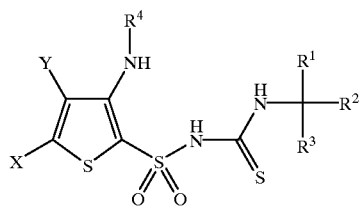
(X)

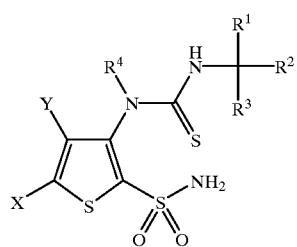
(XI)

(b) treating said structures X or XI by ring-closure to form the compound of claim 1.

29. The method according to claim 28, wherein the compounds of formula X or XI are treated by ring closure by treatment with phosgene in a suitable solvent.

30. A method for preparing the compound of claim 1 comprising
(a) reacting a compound of formula VIII

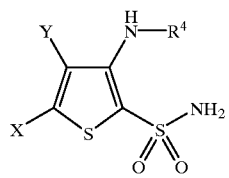
(VIII)

wherein X and Y are independently hydrogen, halogen, perhalomethyl, $C_{1-6}$-alkyl or $C_{1-6}$-alkoxy and $R^4$ is $R^5OC(=O)$, wherein $R^5$ is $C_{1-6}$-alkyl with a compound of formula IX

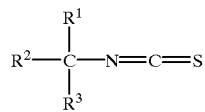
(IX)

wherein $R^1$, $R^2$ and $R^3$ independently are $C_{1-6}$-alkyl, $C_{2-6}$-alkenyl, $C_{2-6}$-alkynyl, $C_{3-6}$-cycloalkyl, carboxy, $C_{1-6}$-alkoxycarbonyl or aryl, all of which are optionally being mono- or polysubstituted with halogen, hydroxy, oxo or aryl; or $R^1$ is defined above and $R^2$—C—$R^3$ form a $C_{-3-6}$ cycloalkyl group, optionally being mono- or polysubstituted with $C_{1-6}$-alkyl, perhalomethyl, halogen, hydroxy or aryl; or $CR^1\ R^2\ R^3$ form a 4- to 12-membered bicyclic or tricyclic carbocyclic system, optionally being mono- or polysubstituted with $C_{1-6}$-alkyl, perhalomethyl, halogen, hydroxy or aryl to form an adduct which may have either of the two structures X or XI or mixtures thereof;

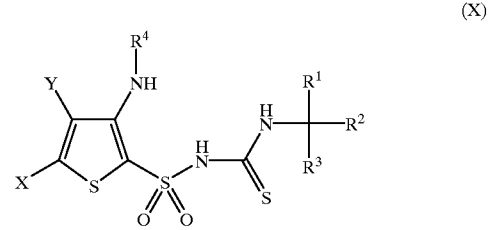
(X)

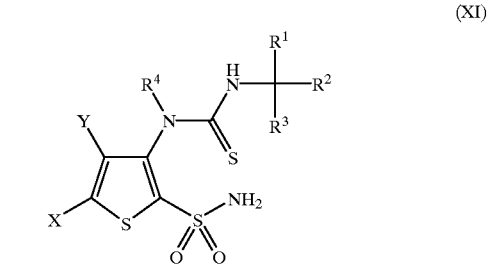
(XI)

(b) treating said structures X or XI by ring-closure to form the compound of formula XII and

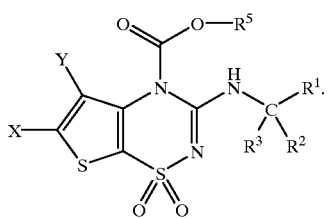
(XII)

(c) hydrolyzing and subsequently decarboxylating the compound of claim XII by heating the said compound in aqueous base.

* * * * *